United States Patent [19]
Hostetler et al.

[11] Patent Number: 6,002,029
[45] Date of Patent: Dec. 14, 1999

[54] ANTIVIRAL PRODRUGS

[76] Inventors: Karl Y. Hostetler, 14024 Rue St. Raphael, Del Mar, Calif. 92014; Ganesh D. Kini, 10153 Camino Ruiz #1, San Diego, Calif. 92126

[21] Appl. No.: 08/986,881

[22] Filed: Dec. 8, 1997

Related U.S. Application Data

[62] Division of application No. 08/340,161, Nov. 15, 1994, Pat. No. 5,696,277.

[51] Int. Cl.$^6$ ...................... C07C 231/00; C07C 315/00; C07F 9/02; A01N 61/00

[52] U.S. Cl. ................................ 554/49; 554/78; 554/85; 554/88; 554/101; 558/152; 558/169; 558/170; 558/180; 558/181; 558/182; 514/1; 568/8; 568/13; 568/18; 568/20; 568/37; 568/45; 568/671

[58] Field of Search ................................ 514/1; 558/152, 558/169, 170, 180, 181, 182; 554/49, 78, 88, 85, 101; 568/8, 13, 18, 20, 37, 45, 671

[56] References Cited

U.S. PATENT DOCUMENTS

| | | | |
|---|---|---|---|
| 4,215,113 | 7/1980 | Eriksson et al. | 424/212 |
| 4,339,445 | 7/1982 | Eriksson et al. | 424/212 |
| 4,386,081 | 5/1983 | Helgstrand et al. | 424/212 |
| 4,591,583 | 5/1986 | Helgstrand et al. | 514/120 |
| 4,665,062 | 5/1987 | Eriksson et al. | 514/20 |
| 4,771,041 | 9/1988 | Eriksson et al. | 514/20 |
| 5,072,032 | 12/1991 | McKenna | 562/9 |
| 5,194,654 | 3/1993 | Hostetler et al. | 558/152 |
| 5,696,277 | 12/1997 | Hostetler et al. | 554/49 |

OTHER PUBLICATIONS

Bangham, A. D. et al. "Diffusion of univalent ions across the lamellae of swollen phospholipids" J. Mol. Biol. 13:238–252, 1965.

Bose et al. "A facile replacement of hydroxyl by halogen with inversion" Tetrahedron Letters 40:3937–3940, 1973.

Chrisp et al. "Foscarnet: A review of its viral activity, pharmacokinetic properties and therapeutic use in immunocompromised patients with cytomegalovirus retinitis" Drugs 41(1):104–129, 1991.

Corey et al. A direct total synthesis of thromboxane B, (+). Tetrahedron Letter, 9:785–788, 1977.

Evans et al. "Thiosilanes a promising class of reagents for selective carbonyl protection" J. Amer. Chem. Soc. 99:5009–5017, 1977.

Kluge et al. Synthesis of prostaglandin models and prostaglandins by conjugate addition of a functionalized organocopper reagent. J. Amer. Chem. Soc. 94:7827–7832, 1972.

Kobayashi et al. Studies of organic fluorine compounds IV 1)conversion of alcohols to fluoride by diphenyltrifluorophosphorane. Chem. Pharm. Bull. 16:1784–1787, 1968.

Lambert et al Synthesis and antiviral activity of phosphonoacetic and phosphonoformic acid esters of 5–bromo–2'–deoxyuridine and related pyrimidine nucleosides and acylclonucleosides. American chemical society 32:367–374, 1989.

Larder et al. "HIV with reduced sensitivity to zidovudine (AZT)isolated during prolonged therapy". Reports 243:1731–1734, 1989.

Larder et al. "Susceptibilities of zidovudine–susceptible and resistant human immunodeficiency virus isolates to antiviral agents determined by using a quantitative plaque reduction assay." Antimicrobial Agents and Chemotherapy 34(3):436–441, 1990.

Szoka et al. "Increased efficacy of phosphonoformated and phosphonoacetate inhibition of herpes simplex virus type 2 replication by encapsulation in liposomes." Antimicrobial Agents and Chemotherapy 32(6):858–864, 1988.

Kini et al. "Alkoxy propane prodrugs of foscarnet: effect of alkyl chain length on in vitro antiviral activity in cells infected with HIV–1, HSV–1 and HCMV" Antiviral Research vol. 36, pp. 43–53, 1997.

Kini et al. "Synthesis and antiviral activity of 1–O–octadecyl–2–O–alkyl–sn–glycerol–3–foscarnet conjugates in human cytomegalovirus–infected cells." Antiviral Research vol. 36, pp. 115–124, 1997.

Berge, S. et al. (1977) Pharmaceutical salts. Journal of Pharmaceutical Sciences 66(1):1–19.

Chesebro, B. et al. (1988) Development of a sensitive quantitative focal assay for human immunodeficiency virus infectivity. Journal of Virology 62(10):3779–3788.

Fukuzawa, A. et al. (1987) Synthesis of (+)–prepinnaterpene, a bromoditerpene from the red alga *laurencia pinnata yamada*. Tetrahedron Letter 28(37):4303–4306.

Helgstrand, E. et al. (1978) Trisodium phosphonoformate, a new antiviral compound. Science 201:819–821.

Kim, et al. (1983) Preparation of multivesicular liposomes. Biochimica et Biophysica Acta 728:339–348.

Leserman, L. et al. (1980) Targeting to cells of fluorescent liposomes covalently coupled with monoclonal antibody or protein A. Nature 288:602–604.

Mayer, L. et al. (1986) Vesicles of variable sizes produced by a rapid extrusion procedure. Biochimica et biophysica Acta 858:161–168.

Mayhew, E. et al. (1984) Characterization of liposomes prepared using a microemulsifier. Biochimica et Biophysica Acta 775:169–174.

(List continued on next page.)

*Primary Examiner*—Jezia Riley
*Attorney, Agent, or Firm*—Pillsbury Madison & Sutro LLP; Anita M. Kirkpatrick

[57] ABSTRACT

Lipid prodrugs of phosphonoacids and their analogs that have increased antiviral activity over the parent drugs in inhibiting cytomegalovirus and other susceptible viruses.

17 Claims, No Drawings

OTHER PUBLICATIONS

Norén, J. et al. (1983) Synthesis of esters of phosphonoformic acid and their antiherpes activity. J. Med. Chem. 26:264–270.

Olson, F. et al. (1979) Preparation of liposomes of defined size distribution by extrusion through polycarbonate membranes. Biochimica et Biophysica Acta 557:9–23.

Seela, F. et al. (1987) Oligodeoxyribonucleotides containing 1.3–propanediol as nucleoside substitute. Nucleic Acids Research 15(7):3113–3129.

Stec, W. et al. (1976) Organophosphorus compounds of sulfur and selenium. Stereochemistry of oxidation of thiono–and selenophosphoryl compounds with hydrogen peroxide. J. Org. Chem. 41(2):233–238.

Szoka, F. et al. (1978) Procedure for preparation of liposomes with large internal aqueous space and high capture by reverse–phase evaporation. Proc. Natl. Acad. Sci. 75(9):4194–4198.

ANTIVIRAL PRODRUGS

This application is a divisional of U.S. Ser. No. 08/340,161, filed Nov. 15, 1994, now U.S. Pat. No. 5,696,277.

The present invention relates generally to lipid derivatives of antiviral agents. It relates particularly to lipid prodrugs of phosphonoacids and their use in the treatment of viral infections.

BACKGROUND OF THE INVENTION

Phosphonoacetate and phosphonoformate were first synthesized in 1924 (Nylén, Chem. Berichte 57:1023); however, the ability of these compounds to inhibit viral enzymes selectively was not immediately demonstrated. Helgstrand, et al. Science 201:819–821 (Sep. 1, 1978) disclosed that both phosphonoacetic acid and phosphonoformic acid inhibit several DNA polymerases and preferentially inhibit several viral DNA polymerases. Phosphonoformate and phosphonoacetate are presently known to selectively inhibit the DNA polymerase of many viruses, including human cytomegalovirus (HCMV), herpes simplex virus (HSV) and the reverse transcriptase of human immunodeficiency virus (HIV). Chrisp and Clissold (1991) Drugs 41:104 review the pharmacology of these agents. Phosphonoacetate is too toxic for use in humans, but phosphonoformate (Foscavir, Astra) is approved for human use in HCMV-infected AIDS patients. However, it is not highly potent, requires prolonged intravenous administration and has substantial toxicity to the kidney and other organs. Ericksson, et al., U.S. Pat. Nos. 4,215,113; 4,339,445; 4,665,062; 4,771,041 teach the use of phosphonoformic acid as the selective agent in treating viral infections, including herpes virus type I and II and cytomegalovirus, in treating cancer caused by virus, and also opposing transformation of cells caused by oncogenic viruses.

Derivatized forms of phosphonoacids and pharmaceutical formulations comprising these compounds are known. U.S. Pat. No. 5,072,032 to McKenna discloses thiophosphonoacids; U.S. Pat. Nos. 4,386,081 and 4,591,583 to Helgstrand et al. disclose phosphonoformic acid esters of alkyl, alkylene, alkoxy and related cyclic and aromatic groups and some of these are shown to inhibit herpes virus and the functions and intracellular multiplication of influenza virus. U.S. Pat. No. 5,194,654 to Hostetler et al, discloses phospholipid derivatives of phosphonoacids, their incorporation into liposomes and their use as selective antiviral and antiretroviral agents.

There is a continuing need for less toxic, more selective and more effective antiviral prodrugs of the phosphonoacids.

SUMMARY OF THE INVENTION

According to the invention there are provided compounds having the structure [I] and the substituents R1, R2, R3, Y, Z, A⁻, m, and n as defined herein. According to a preferred embodiment of the invention, m is 0. In yet another preferred embodiment X is oxygen.

According to other preferred embodiments of the invention, R1 is an O-alkyl group; particularly preferred are compounds wherein R1 is an O-octadecyl group. Also preferred are compounds wherein R2 is an O-benzyl group or an OCH₃ group.

In yet another preferred embodiment, Z is R3 and R3 is an ethyl group. Particularly preferred compounds are 1-O-octadecyl-1,3-propanediol-3-phosphonoacids; 1-O-octadecyl-1,3-propanediol-3-thiophosphonoacids; 1-O-octadecyl-2-O-methyl-sn-glycero-3-phosphonoacids; 1-O-octadecyl-2-O-methyl-sn-glycero-3-thiophosphonoacids; 1-O-octadecyl-2-O-benzyl-sn-glycero-3-phosphonoacids; 1-O-octadecyl-2-O-benzyl-sn-glycero-3-thiophosphonoacids. 1-O-octadecyl-sn-glycero-3-phosphonoacid ethyl esters; 1-O-octadecyl-sn-glycero-3-thiophosphonoacid ethyl esters; 1,2-dimyristoyl-sn-glycero-3-thiophosphonoacid ethyl esters; 1,2-dimyristoyl-sn-glycero-3-phosphonoacid ethyl esters; 1,2-dimyristoyl-sn-glycero-3-thiophosphonoacid ethyl esters;

According to another aspect of the invention there are provided compounds having the general structure of Formula [II] wherein R1, R2, R3, Y, Z, A⁻ m and n are as defined herein. Preferred compounds among this group are 1-O-octadecyl-sn-glycero-3-phosphonoacetates; and 1-O-octadecyl-2-O-benzyl-sn-glycero-3-phosphonoformates.

According to yet another aspect of the invention there are provided 2-carbon analogues of the compounds of the invention. Preferred compounds according to this embodiment are 1-O-octadecyl-1,2-ethanediol-2-phosphonoacetate; 1-O-octadecyl-1,2-ethanediol-2-phosphonoformate; 1-O-octadecyl-1,2,ethanediol-(C)-phosphonoformate; and 1-O-octadecyl-1,2,ethanediol-(C)-phosphonoacetate.

According to yet another aspect of the invention there are provided liposomes or other lipid vesicles formed in part from a compound according to the invention. The invention also provides methods for treating a viral or retroviral infection in a mammal, comprising administering an effective amount of a compound according to the invention to the mammal. These methods can further comprise the co-administration of an antiviral nucleoside analogue, a viral protease inhibitor or other antiviral agent.

DETAILED DESCRIPTION OF THE INVENTION

It is an object of the invention to provide lipid prodrugs of the phosphonoacids that retain the pharmacological effects of the parent compounds. Unexpectedly, it has been found that the compounds of the present invention have advantageous pharmacological effects over previously known prodrugs of this type. The invention accordingly provides a series of improved prodrugs of phosphonoformate and phosphonoacetate and their analogs having substantial increases in antiviral activity over the parent compounds against human cytomegalovirus (HCMV), herpes simplex virus (HSV), and human immunodeficiency virus (HIV-1). This enhanced antiviral activity can be demonstrated in cell culture, for example, by means of the in vitro susceptibility assays described in Examples 17 through 20.

The compounds of the invention have the general formula [I]:

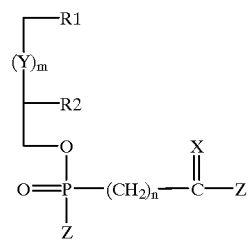

wherein
R1 is
O-Alkyl $C_1$ to $C_{24}$, 0–6 double bonds;
S-Alkyl $C_1$ to $C_{24}$, 0–6 double bonds;

O-Acyl $C_1$ to $C_{24}$, 0–6 double bonds; or
S-Acyl $C_1$ to $C_{24}$, 0–6 double bonds;

each R2 is independently OH, H, a halogen such as fluorine, chlorine, iodine and bromine, $OCH_3$, O-benzyl, SH, $SCH_3$, or $NH_2$;
O-Acyl $C_1$ to $C_{24}$, 0–6 double bonds;
S-Acyl $C_1$ to $C_{24}$, 0–6 double bonds;
O-Alkyl $C_1$ to $C_{24}$, 0–6 double bonds;
S-Alkyl $C_1$ to $C_{24}$, 0–6 double bonds;
N-Acyl $C_1$ to $C_{24}$, 0–6 double bonds; or
N-Alkyl or N-dialkyl, $C_1$ to $C_{24}$, 0–6 double bonds;

Z is OR3 when the compound of formula (I) is esterified or Z is $O^-A^+$ when [I] is in the form of a salt or a combination thereof;

R3 is independently selected from the group consisting of substituted or unsubstituted linear $C_1$ to $C_6$ alkyl groups, substituted or unsubstituted branched $C_3$ to $C_6$ alkyl groups, $CH_3(CH_2)_nNH_2$, wherein n is 0 to 8, $(CH_3)_3N^+CH_2CH_2OH$, $HOCH_2CH_2NH_2$, $HOCH_2CH(NH_2)CO_2H$, $C_6H_{12}O_6$, $CH_2OHCHOHCH_2OH$; $CH_2Ph$; pentoses, hexoses and their corresponding alcohols;

Each $A^+$ is independently selected from the group consisting of $H^+$; $Na^+$, $NH_4^+$; amines selected from the group consisting of mono-, di-, and trialkylamines; and other physiologically acceptable cations; and n=0 or 1.

Physiological cations can be organic or metallic, selected according to the criteria disclosed in Berge, S M et al. J. Pharm. Sci. 66(1):1–19. Preferred cations are sodium or potassium ions.

Y is $CH_2$—R2; m=0–6; and when m≧1, Y is a $CH_2$-R2 group, wherein R2 is independently selected from the group defined above; X is O, S, or Se; and n is 0 or 1.

The alkyl and acyl groups of R1, and R2 can be substituted or unsubstituted, linear or branched. The result of the independent selection of R2 groups on each of the internal Y carbons when m>0 is that the molecule may comprise from 2 to 7 different R2 groups.

Alternatively, the compounds of the invention have the formula II:

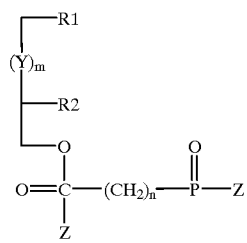

wherein R1, R2, R3, Y, Z, $A^+$, m and n are defined as above. The compounds of formula II differ from those of formula I by having the phosphonoacid moiety coupled to the lipid moiety through a carboxy rather than a phosphate linkage.

Synthesis of Improved Prodrugs of the Phosphonoacids

The compounds that are synthesized are outlined in Scheme I with the various substituents on C1, C2 and C3 of the glycerol, and similarly in Schemes II and III for compounds wherein $(Y)_m$ is $(CH_2—R2)_m$ and m≧1.

Identification of Starting Materials and Products

The phosphonoacids to which various lipid moieties are coupled in the preparation of the lipid prodrugs of the invention are designated by acronyms, as follows:
n=0, X=O (PFA) Phosphonoformic acid
n=0, X=S (PFSA) Thiophosphonoformic acid
n=0, X=Se (PFSeA) Selenophosphonoformic acid
n=1, X=O (PAA) Phosphonoacetic acid
n=1, X=S (PASA) Thiophosphonoacetic acid
n=1, X=Se (PASeA) Selenophosphonoacetic acid The various lipid prodrug derivatives are designated herein by acronyms derived from those above, and defined in the legends of Tables I–IV.

Synthesis Procedures

Lipid prodrugs of the phosphonoacids listed above are prepared according to the procedures described in Examples 1–16. A synthesis flow diagram particularly relevant to the synthesis of compounds wherein m=0 and Y is absent is set forth in Scheme I; flow diagrams particularly relevant to the chemical synthesis of compounds wherein m>0 and Y is present are set forth in Schemes II and III.

Antiviral Activity

The antiviral activity of various lipid derivatives of phosphonoacids according to the invention was determined in cultures of human cell lines infected with HCMV, HSV, or HIV-1 as described in Example 17. The results are shown in Tables I–IV. The predictive value of in vitro susceptibility testing for viral infections is discussed by Kern, E R (1990) Preclinical evaluation of antiviral agents: In vitro and animal model testing. Galasso, G. et al. eds. Antiviral Agents and Viral Disease of Man, 3rd Edition, Raven Press, New York pp. 87–123.

The most preferred compounds which exhibit greatly increased antiviral activity (Tables I–IV) have 1-O-alkyl groups at R1, and hydroxyl, O-methyl or O-benzyl at R2.

Antiviral activity of the improved phosphonoacid prodrugs against human cytomegalovirus-infected MRC5 human lung fibroblast-cells is shown in Tables I and II. The most preferred prodrugs of phosphonoformate (Table I) have remarkable increases in antiviral activity. Previous attempts to produce prodrugs of phosphonoformate with increased activity have identified a few compounds which have very small increases in activity, but no compound having increases in activity over PFA greater than 1.9 fold have been shown previously (Norén, J. O., et al., J. Med. Chem., 26:264–270, 1983). The most active PFA prodrugs, B-PFA, BB-PFA, and MB-PFA, exhibit 107-, 72- and 38-fold increases in activity and represent the most active PFA-containing compounds yet reported. These compounds have a 1-O-alkyl group at the R1 position of glycerol and either a hydroxyl, -O-benzyl or -O-methyl function at the R2 of glycerol. Prodrugs having H, halogen or amino at R2 will also be highly active and substitution at X of S or Se for O will provide similar results.

B-PFA-OEt retains substantial activity (16-fold increase over PFA) with a carboxyethyl ester at the R3 position. Other ester substituents at R3 which will provide excellent activity include choline, ethanolamine, glycerol and inositol. These compounds bear a resemblance to naturally occurring lysophospholipids and may be converted to active drugs inside the target cells more readily than carboxyethyl esters.

Similar results were obtained in human cytomegalovirus-infected cells with the phosphonoacetate series of compounds shown in Table II. Here the order of activity was slightly different with B-PAA, MB-PAA and BB-PAA exhibit 100-, 36- and 24-fold increases in activity compared with free PAA. When the phosphonoacetic acid is linked to glycerol at the sn-3 hydroxyl in a carboxyester linkage as in BB-(C)-PAA, nearly full antiviral activity is retained (16-fold increase vs PAA). Glycerol-PAA derivatives with two acyl chains (DMG-PAA), or two phosphorus residues and two acyl esters (DMP-PAA and DPP-PAA), did not exhibit substantially increased activity (1.2-, 0.24- and 0.28-times the activity of PAA, respectively).

The improved PFA prodrugs also exhibit greatly increased activity versus PFA in herpes simplex virus-1 infected human lung fibroblasts (Table III). MB-PFA, B-PFA and BB-PFA are 72-, 43- and 34-times more active than PFA and represent the most active PFA derivatives yet reported. The order of activity is slightly different from that observed with human cytomegalovirus; MB-PFA is the most active compound followed by B-PFA and BB-PFA. Similar results were obtained with human immunodeficiency virus-1 infected cells in vitro (Table IV). With HIV-1, MB-PFA was the most active compound followed by B-PFA and BB-PFA; the compounds were 104-, 37- and 9-fold more active than PFA in HIV-infected HT4-6C cells and represent the most active anti-HIV derivatives of PFA reported. MB-PFA was more active than B-PFA to a statistically significant degree (Table IV).

Therapy of Viral Diseases

The lipid derivatives of phosphonoacids disclosed herein are useful in treating diseases caused by viruses such as influenza, herpes simplex virus (HSV), human herpes virus 6, cytomegalovirus (CMV), hepatitis B virus, Epstein-Barr virus (EBV), and varicella zoster virus (VZV). They are useful in the treatment of AIDS and other retroviral diseases, as well.

Lipid derivatives of antiviral phosphonoacids may be applied topically to the skin, eyes or mucous membranes or into the interior of the body, for treating susceptible virus infections in man and animals. They can be introduced internally, for example orally, intratracheally or otherwise by the pulmonary route, enterally, rectally, nasally, vaginally, lingually, intravenously, intra-arterially, intramuscularly, intraperitoneally, intradermally, or subcutaneously. The present pharmaceutical preparations can contain the active agent alone, or can contain further pharmaceutically valuable substances. For example, formulations comprising lipid phosphonoacid prodrugs of the invention can additionally comprise another antiviral agent, such as for example, a viral protease inhibitor, or an antiviral nucleoside analogue. They can further comprise a pharmaceutically acceptable carrier.

Lipid derivatives of antiviral agents may have a prolonged antiviral effect as compared to the lipid-free agents; therefore they provide therapeutic advantages as medicaments even when not incorporated into liposomes. These phosphonoacid prodrug antiviral agents may be used alone or in combination with antiviral nucleosides as given conventionally. The use of combination therapy may greatly reduce the tendency for drug resistant HIV mutant strains to appear and would therefore increase the likelihood of stopping the progression of HIV infection. The same argument would hold equally well in treating cytomegalovirus or herpes virus infections with regard to the likelihood of developing resistant strains.

Formulations

Pharmaceutical preparations containing lipid derivatives of antiviral phosphonoacids are produced by conventional dissolving and lyophilizing processes to contain from approximately 0.1% to 100%, preferably from approximately 1% to 90% of the active ingredient. They can be prepared as ointments, salves, tablets, capsules, powders or sprays, together with effective excipients, vehicles, diluents, fragrances or flavor to make palatable or pleasing to use.

Formulations for oral ingestion are in the form of tablets, capsules, pills, ampules of powdered active agent, or oily or aqueous suspensions or solutions. Tablets or other non-liquid oral compositions may contain acceptable excipients, known to the art for the manufacture of pharmaceutical compositions, comprising diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract. The preparations can also comprise bile salts and detergents.

Aqueous suspensions may contain the active ingredient in admixture with pharmacologically acceptable excipients, comprising suspending agents, such as methyl cellulose; and wetting agents, such as lecithin, lysolethicin or long-chain fatty alcohols. The said aqueous suspensions may also contain preservatives, coloring agents, flavoring agents and sweetening agents in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

Liposomal Formulations

If desired, the compounds can be incorporated into liposomes by any of the reported methods of preparing liposomes for use in treating viral diseases such as, but not limited to HCMV, HSV, and HIV-1. The present invention may utilize the antiviral phosphonoacid derivatives noted above incorporated in liposomes in order to direct these compounds to macrophages, monocytes, other cells and tissues and organs which take up the liposomal composition. The liposome-incorporated phosphonoacid derivatives of the invention can be used to treat HCMV, HSV or AIDS patients by parenteral administration, enhancing delivery of the antiviral compound to macrophages and monocytes, an important reservoir of viral infections. This will allow for the efficacious use of lower doses of the modified phosphonoacids, reducing toxicity of the compound. Ligands may also be incorporated to further focus the specificity of the liposomes.

The derivatives described have several unique and novel advantages over the liposomal water soluble phosphonoformates. First, they can be formulated in liposomes to much higher ratios of drug to lipid because they are incorporated into the wall of the liposome instead of being located in the aqueous core compartment. Secondly, the liposomes containing the lipophilic phosphonoformate derivatives noted above do not leak during storage, providing improved product stability. Furthermore, these compositions may be lyophilized, stored dry at room temperature, and reconstituted for use, providing improved shelf life. They also permit efficient incorporation of antiviral compounds into liposomal formulations without significant waste of active compound. A further advantage is that the compositions used in vivo treatment cause a larger percentage of the administered antiviral lipid-phosphonoacid conjugate to reach the intended target. At the same time the use of the compositions reduces the amount being taken up by the kidney and bone, thereby decreasing the toxic side effects of the phosphonoacid drug. The toxic side effects of the phosphonoformates may be further reduced by targeting the liposomes in which they are contained to actual or potential sites of infection by incorporating ligands into the liposomes. The liposome-incorporated lipid-phosphonoacid conjugate is administered to patients by any of the known procedures utilized for administering liposomes. The liposomes can be administered intravenously, intraperitoneally, intramuscularly, intravitreally or subcutaneously as a buffered aqueous solution. Any pharmaceutically acceptable aqueous buffer or other vehicle may be utilized so long as it does not destroy the liposome structure or the activity of the lipid phosphonoacid analogue. One suitable aqueous buffer is isotonic sorbitol containing 5 mM sodium phosphate with a pH of about 7.4, or other physiological buffered salt solutions.

The therapeutically effective amount of the lipid derivatives is determined by reference to the recommended dosages of the active antiviral phosphonoacid, bearing in mind that, in selecting the appropriate dosage in any specific case, consideration must be given to the patient's weight, general health, metabolism, age and other factors which influence response to the drug. The dosage for a mammal, including a human, may vary depending upon the extent and severity of the infection and the activity of the administered compound. Dosage levels of liposomal lipid analogs of phosphonoacids will be about the same as for the phosphonoacid itself. Dosage levels for the phosphonoacids through conventional administration by intravenous infusion are well established (Lambert, R., et al. (1989) J. Med. Chem. 32:367–374; Szoka, F. and Chu, C-J., Antimicrobial Agents and Chemotherapy: 32(6) 858–864 (1988); Ericksson et al. U.S. Pat. No. 4,771,041). Foscarnet is administered by i.v. infusion at 200 mg/kg/day for treatment of HCMV in humans.

The phosphonoacid prodrugs of the invention are administered to the patient on a daily basis in an oral dose of about 0.1 mg/kilogram to 1000 mg/kilogram and more preferably from about 1 mg/kilogram to about 400 mg/kilogram. The parenteral dosage will be appropriately 20 to 100% of the oral dose.

Liposome Preparation

After synthesis and purification, the lipid derivative of the phosphonoacid is incorporated into liposomes, or other suitable carrier. The incorporation can be carried out according to well known liposome preparation procedures, such as sonication and extrusion. Suitable conventional methods of liposome preparation include, but are not limited to, those disclosed by Bangham, et al. (Bangham, A. D., Standish, M. M. and Watkins, J. C. (1965) J. Mol. Biol., 23: 238–252.) Olson, et al. (Olson, F., Hunt, C. A. Szoka, F. C., Vail, W. J. and Papahadjopoulos, D. (1979) Biochim, Biophys. Acta, 557: 9–23.), Szoka, F. and Papahadjapoulos, D. (1978) Proc. Nat. Acad. Sci. 75: 4194–4198, Mayhew, E. et al. (1984) 775: 169–175), Kim, S. et al. (1983) Biochim. Biophys. Act, 728: 339:348, and Mayer, et al. (1986) Biochim. Biophys. Acta, 858: 161–168.

The liposomes may be made from the lipid derivatives of phosphonoacids alone or in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol. Synthetic phospholipids that may also be used, include, but are not limited to: dimyristoylphosphatidylcholine, dioleoylphosphatidylcholine, dipalmitoylphosphatidylcholine and distearoylphosphatidycholine, and the corresponding synthetic phosphatidylethanolamines and phosphatidylglycerols. Cholesterol or other sterols, cholesterol hemisuccinate, glycolipids, cerebrosides, fatty acids, gangliosides, sphingolipids, 1,2-bis(oleoyloxy)-3-(trimethyl ammonio)propane (DOTAP), N-[1-(2,3-dioleoyl)propyl]-N, N,N-trimethylammonium chloride (DOTMA), and other cationic lipids may be incorporated into the liposomes, as is known to those skilled in the art. The relative amounts of phospholipid and additives used in the liposomes may be varied if desired. The preferred ranges are from about 60 to 90 mole percent of the phospholipid; cholesterol, cholesterol hemisuccinate, fatty acids or cationic lipids may be used in amounts ranging from 0 to 50 mole percent. The amounts of antiviral phosphonoacids incorporated into the lipid layer of liposomes can be varied with the concentration of their lipids ranging from about 0.01 to about 50 mole percent.

Using conventional methods, approximately 20 to 30% of the free phosphonoacid present in solution can be entrapped in liposomes; thus, approximately 70 to 80% of the active compound is wasted. In contrast, where the lipid phosphonoacid is incorporated into liposomes, virtually all of the antiviral compound is incorporated into the liposome, and essentially none of the active compound is wasted.

The liposomes with the above formulations may be made still more specific for their intended targets with the incorporation of monoclonal antibodies or other ligands specific for a target. For example, monoclonal antibodies to the CD4 (T4) receptor may be incorporated into the liposome by linkage to phosphatidylethanolamine (PE) incorporated into the liposome by the method of Leserman, L. et al. (1980) Nature 288:602–604.

EXPERIMENTAL PROCEDURES

The chemical reactions described below are generally disclosed in terms of their general application to the preparation of the lipid prodrugs of the invention. Occasionally, the reaction may not be applicable as described to each prodrug within the disclosed scope. The compounds for which this occurs will be readily recognized by those skilled in the art. In all such cases, either the reactions can be successfully performed by conventional modifications known to those skilled in the art, that is, by changing to alternative conventional reagents, or by routine modification of reaction conditions. Alternatively, other reactions disclosed herein or otherwise conventional will be applicable to the preparation of the compounds of the invention. In all preparative methods, all starting materials are known or readily preparable from known starting materials.

Without further elaboration, it is believed that one skilled in the art can, using the preceding description, utilize the invention to its fullest extent. The following preferred embodiments are therefore to be construed as merely illustrative and not limitative of the remainder of the disclosure in any way whatsoever. All the temperatures indicated in the Examples are in degrees Celsius and are uncorrected.

The present invention is described below in detail using the following examples, but the methods disclosed are applicable for the preparation of all phosphonoacids covered by the scope of the invention and are not limited to the examples.

EXAMPLE 1

Synthesis of 1-O-alkyl-2-halo-sn-glycero-3-phosphonoformate analogs and 1-O-alkyl-2-amino-sn-glycero-3-phosphonoformate analogs The stereo-controlled synthesis of analogs 1-O-alkyl-2-halo-sn-glycero-3-phosphonoformate is outlined in Scheme 1. 2,3-Isopropylidine-sn-glycerol, upon treatment with the appropriate alkylmethane sulfonate, leads to the intermediate 2. Removal of the isopropylidine group by treatment with acetic acid followed by tritylation with trityl chloride and pyridine results in compound 3, with a free 2-hydroxyl group. Treatment of 3 with n-halosuccimide and triphenyl phosphine according to the procedure of Bose and Lal [(1973, Tetrahedron Lett. 40:3937) will lead to intermediate 4. The replacement of the hydroxyl group with halogen proceeds with complete inversion ($SN_2$ displacement) and in yields from 65–95%. Removal of the trityl group with trifluoroacetic acid in dichloromethane leads to the halo compound 5. Reaction of 5 with carbethoxyphosphodichloridate results in the phosphonoformic acid analog 6.

While this procedure works when X is Cl, Br and I, a slightly different approach is needed for the analog when X=F. Treatment of the intermediate 3 with diphenyltrifluorophosphorane according to a procedure reported by Kobayashi and co-workers (1968, Chem. Pharm. Bull. 16(9):1784) leads to the conversion of alcohol 3 to the fluorinated compound 4 in good yields. Subsequent steps to the fluoro analogs of 6 are identical to those described earlier.

Treatment of bromo intermediate 4 described in Scheme I with liquid ammonia in a steel bomb will result in amination at the 2-position. Treatment of the resulting 2-amino compound with benzyl bromide will protect the 2-amino group. Subsequent steps will be identical to those described in Scheme I up to intermediate 6. The benzyl protecting group can be removed at this point by hydrogenolysis with Pd/C.

Treatment of the amino intermediate with acyl chloride will result in the N-acyl compound. Alternatively, treatment of the bromo intermediate 4 with mono or dialkyl amine will result in the monoalkyl amino and dialkylamino derivatives.

The procedures described above can be carried out with readily available starting materials, the methodology is well documented and those skilled in the art can recognize the modifications needed in starting materials and methods to synthesize the 2-amino analogs that have been listed.

EXAMPLE 2

Synthesis of Thiophosphonoacids and Their Lipid Prodrugs

Thiophosphonoformic acid is synthesized according to the procedure of McKenna (U.S. Pat. No. 5,072,032) by the reaction of trimethyl phosphonoformic acid with Lawesson's reagent [2,4-bis(4-methoxyphenyl)-1,3-dithia-2,4-diphosphetane 2,4-disulfide]. Thiophosphonoacetic acid is also synthesized in a similar manner.

Selenophosphonoformic acid can be synthesized by treatment of trimethylphosphonoformic acid with elemental selenium by adaptation of procedures reported by Stec and co-workers (1976, Stec, W. J., Okruszek, A and Michalski, J. J. Org. Chem. 41, 233), and by Buina et al (1979, Buina, N. A.; Sibgatullina, F. G.; Neureldinor, I. A. Izv. Akad. Nauksssr., Ser. Khim. 10, 2362). Selenophosphonoacetic acid can also be synthesized in a similar manner. The selenoacids can then be converted to the corresponding lipid prodrugs by procedures identical to those for the oxo- and thio-analogues.

The synthesis of batyl-thiophosphonoformic acid (PFSA) was carried out in a manner similar to the synthesis of batyl-phosphonoformic acid, with some modifications. 1-O-Octadecyl-2-O-benzyl-sn-glycerol, purchased from Bachem (Basel, Switzerland), was coupled to thiophosphonoformic acid ethyl ester using dicyclohexylcarbodiimide. After purification by silica gel chromatography, the PFSA-ethyl ester was debenzylated with Pd/C and cyclohexene. This procedure, reported in (1977, J. Chem. Soc., Perkin Trans. 1, 490) can be used for hydrogenolysis of compounds containing sulfur. The PFSA was obtained by base hydrolysis of the debenzylated ester. Batyl-thiophosphonoacetic acid was synthesized in a similar manner.

EXAMPLE 3

Synthesis of 1-O-octadecyl-1,3-propanediol-3-phosphonoformate and 1-O-octadecyl-1,2-ethanediol-2-phosphonoformate Preparation of 1-O-octadecyl-1,3-propanediol 1-O-trityl-1,3-propanediol, synthesized according to the procedure of Sela, et al. (1987) Nucleic Acids Research 15:3124, was treated with octadecylmethanesulfonate (NuChek Prep, Inc.) in the presence of sodium hydride in dimethylformamide. The product, 1-O-octadecyl-3-O-trityl propanediol, was isolated and purified by flash chromatography. The trityl protecting group was removed by treatment with trifluoroacetic acid in dichloromethane to yield 1-O-octadecyl-1,3-propanediol.

To a solution of carbethoxyphosphodichloridate (1.6 mmol) in chloroform (25 ml), cooled to 0° C. in an ice salt bath, was added a solution of 1-O-octadecylpropanediol (1 mmol) in pyridine (15 ml), dropwise with stirring. The mixture was allowed to warm to room temperature and stirred at room temperature overnight. The mixture was cooled, and 1 ml water was added. After stirring at 0° C. for 2 h, the mixture was concentrated in vacuo. The residual oil was flash chromatographed with chloroform-methanol 95:5 as eluent to yield product: 1-O-octadecylpropanediol-3-ethylphosphonoformate.

The ethyl ester was dissolved in 1:1 mixture of ethanol and 0.1N NaOH (50 ml) and sonicated for 15 minutes. The resulting mixture was stirred at 60° C. in an oil bath for 2 h. The mixture was filtered and the filtrate was concentrated to dryness in vacuo. The resulting solid was resuspended in water, cooled and lyophilized to yield target compound.

The corresponding 1,2-ethanediol analogue may be prepared as described in the above method by substituting 1-O-trityl-1,2-ethanediol as the starting material.

EXAMPLE 4

Synthesis of 1-O-octadecyl-1,3-propanediol-3-phosphonoacetate and 1-O-octadecyl-1,2-ethanediol-2-phosphonoacetate To a mixture of 1-O-octadecyl-1,3-propanediol (1 mmol) and phosphonoacetic acid ethyl ester (1.1 mmol) in pyridine, (50 ml) cooled to 0° C. in an ice bath, was added a solution of dicyclohexylcarbodiimide (DCC; 3 mmol) in $CH_2Cl_2$ (20 ml) dropwise with stirring. The mixture was stirred at 0° C. for 2 h and at room temperature overnight. The mixture was concentrated to dryness and the residue was flash chromatographed with chloroform-methanol 95:5 as eluent to yield 1-O-octadecylpropanediol-3-phosphonoacetate ethyl ester.

The ethyl ester was dissolved in a 1:1 mixture of 0.1N NaOH and ethanol (50 ml). The mixture was sonicated for 15 minutes and heated in an oil bath at 60° C. for 2 h. The mixture was filtered, and the filtrate was concentrated in vacuo. The resultant residue was dissolved in water, cooled and lyophilized to yield product as a fluffy white solid.

The corresponding 1,2-ethanediol analogue may be prepared as described in the above method by substituting 1-O-trityl-1,2-ethanediol as the starting material.

EXAMPLE 5

Synthesis of 1-O-octadecyl-1,3-propanediol-3-thiophosphonoformate

To a mixture of 1-O-octadecyl-1,3-propanediol (1 mmol) and ethythiophosphonoformate (1.1 mmol) in pyridine (50 ml) cooled to 0° C. in an ice-salt bath was added a solution of dicyclohexylcarbodiimide (DCC; 3 mmol) in dichloromethane dropwise with stirring. The resulting mixture was stirred at 0° C. for 2 h and at room temperature overnight. The mixture was filtered, and concentrated to dryness in vacuo. The residue was flash chromatographed over silica gel with an increasing gradient of methanol in chloroform as eluent to yield pure product.

The product was dissolved in a mixture of ethanol:0.1N NaOH (1:1, 50 ml) and sonicated for 15 minutes. The resulting mixture was heated at 60° C. for 2 h, filtered and concentrated to dryness. The residue was dissolved in a minimum amount of water and lyophilized to yield the target compound as a fluffy solid.

EXAMPLE 6

Synthesis of 1-O-octadecyl-1,3-propanediol-3-thiophosphonoacetate

To a mixture of 1-O-octadecyl-1,3-propanediol (1 mmol) and ethyl thiophosphonoacetate (1.1 mmol) in $CH_2Cl_2$ (50 ml) cooled to 0° C. in an ice salt bath, was added a solution of dicyclohexylcarbodiimide (3.3 mol), dropwise, with stirring. The resulting mixture was stirred at room temperature overnight. The mixture was concentrated to dryness and flash chromatographed over silica gel with chloroform-methanol (95:5) as eluent to yield pure product.

The ethyl ester was dissolved in a 1:1 mixture of ethanol and 0.1N NaOH (50 ml) and sonicated for 15 minutes. The resulting mixture was heated at 60° C. for 2 h, filtered and concentrated to dryness. The residue was dissolved in minimum amount of water and lyophilized to yield pure compound as a fluffy solid.

EXAMPLE 7

Synthesis of 1-O-octadecyl-2-O-methyl-sn-glycero-3-phosphonoformate

To a solution of carbethoxyphosphodichloridate (1.6 mmol) in chloroform (20 ml), cooled to 0° C. in an ice salt bath was added a solution of 1-O-octadecyl-2-O-methyl-sn-glycerol (1.0 mmol) in pyridine (15 ml) dropwise. The mixture was stirred at room temperature overnight. The mixture was cooled, 2 ml of water added and the resulting mixture stirred at room temperature for 2 h. The reaction mixture was then concentrated in vacuo, and the residue was flash chromatographed over silica gel with chloroform-:methanol as eluent.

The ethyl ester was dissolved in a 1:1 mixture of ethanol and 0.1N NaOH and sonicated for 15 minutes. The mixture was heated with stirring at 60° C. for 2 h, filtered and the filtrate evaporated to dryness. The residue was recrystallized from 25% aqueous ethanol to yield pure product.

EXAMPLE 8

Synthesis of 1-O-octadecyl-2-O-methyl-sn-glycero-3-phosphonoacetate

To a mixture of 1-O-octadecyl-2-O-methyl-sn-glycerol (1 mmol) and phosphonoacetic acid ethyl ester hydrochloride (1 mmol) in pyridine (50 ml), cooled to 0° C. in an ice salt bath was added a solution of dicyclohexylcarbodiimide (3.0 mmol) in $CH_2Cl_2$ (20 ml), dropwise with stirring. The resulting solution was stirred at room temperature overnight. After concentrating in vacuo, the residue was flash chromatographed over silica gel with a gradient of methanol in chloroform as eluent to yield 1-O-octadecyl-2-O-methyl-sn-glycero-3-phosphonoacetic acid ethyl ester.

The ethyl ester was dissolved in a 1:1 mixture of ethanol: 0.1N NaOH (50 ml), and the resulting solution was sonicated for 15 minutes. The solution was then heated in an oil bath at 70° C. for 3 h. The solution was cooled, the resulting solid was filtered off and washed with cold ethanol. The solid was vacuum dried to yield pure product.

EXAMPLE 9

Synthesis of 1-O-octadecyl-2-O-methyl-sn-glycero-3-thiophosphonoformate

To a mixture of 1-O-octadecyl-2-O-methyl-sn-glycerol (1 mmol) and ethyl thiophosphonoformate (1.1 mmol) in dichloromethane (50 ml), cooled to 0° C. in an ice salt bath was added a solution of dicyclohexylcarbodiimide (3 mmol) in $CH_2Cl_2$ (20 ml), dropwise, with stirring. The resulting mixture was stirred at room temperature overnight. The reaction mixture was filtered and concentrated to dryness in vacuo. The residue was flash chromatographed over silica gel with an increasing gradient of methanol in chloroform as the eluting solvent to yield pure 1-O-octadecyl-2-O-methyl-sn-glycero-3-thiophosphonoformic acid ethyl ester.

The ethyl ester was dissolved in a 1:1 mixture of ethanol and 0.1N NaOH (50 ml) and sonicated for 15 minutes. The solution was heated for 2 h at 60° C., filtered, and the filtrate concentrated to dryness. The residue was dissolved in minimum amount of ester and lyophilized to yield the target compound as a fluffy solid.

EXAMPLE 10

Synthesis of 1-O-octadecyl-2-O-methyl-sn-glycero-3-thiophosphonoacetate

To a mixture of 1-O-octadecyl-2-O-methyl-sn-glycerol (1 mmol) and ethyl thiophosphonoacetate (1 mmol) in pyridine (50 ml), was added a solution of dicyclohexylcarbodiimide (DCC; 3.0 mmol) dropwise with stirring. The mixture was stirred at room temperature overnight. Solvent was removed in vacuo, and the residue was flash chromatographed over silica gel with an increasing gradient of methanol in chloroform as eluent to yield pure 1-O-octadecyl-2-O-methyl-sn-glycero-3-thiophosphonoacetic acid ethyl ester.

The ethyl ester was dissolved in a 1:1 mixture of ethanol and 0.1N NaOH (50 ml). The solution was sonicated for 15 minutes and stirred at 65° C. for 2 h. The solution was filtered and the filtrate cooled in the freezer. The resulting solid was filtered off, washed with cold ethanol and dried in vacuo to give pure product.

EXAMPLE 11

Synthesis of 1-O-octadecyl-2-O-benzyl-sn-glycero-3-thiophosphonoformic acid ethyl ester To a solution of 1-O-octadecyl-2-O-benzyl-sn-glycerol (1 mmol) and ethyl thiophosphonoformate (1 mmol) in pyridine (50 ml), cooled to 0° C. in an ice-salt bath, was added a solution of dicyclohexylcarbodiimide (3 mmol) in dichloromethane (20 ml) dropwise with stirring. The mixture was stirred at room temperature overnight. After concentration in vacuo, the residue was chromatographed over silica gel to yield pure target compound.

EXAMPLE 12

Synthesis of 1-O-octadecyl-sn-glycero-3-thiophosphonoformate

1-O-octadecyl-2-O-benzyl-sn-glycero-3-thiophosphonoformic acid ethyl ester (1 mmol) was dissolved in ethanol (25 ml). Pd/C (100 mg) and cyclohexene (5 ml) was added to the solution and the mixture stirred at room temperature overnight. The mixture was filtered and the filtrate was concentrated in vacuo. Purification of the resulting residue by flash chromatography with a gradient of methanol in chloroform resulted in the debenzylated ethyl ester. This ester was dissolved in a 1:1 mixture of ethanol and 0.1 NaOH (50 ml) and the solution was sonicated for 15 minutes. After heating at 60° C. for 2 h, the solution was filtered and the filtrated concentrated in vacuo. The residue was suspended in water, cooled and lyophilized to yield target compound.

EXAMPLE 13

Synthesis of 1-O-octadecyl-2-O-benzyl-sn-glycero-3-thiophosphonoacetic acid ethyl ester To a solution of 1-O-octadecyl-2-O-benzyl-sn-glycerol (1 mmol) and ethyl thiophosphonoacetate (1 mmol) in pyridine (50 ml), cooled to 0° C. in an ice-salt bath, was added a solution of dicyclohexylcarbodiimide (3 mmol) in dichloromethane (20 ml) dropwise with stirring. The mixture was stirred at room temperature overnight, and concentrated to dryness in vacuo. The residue was flash chromatographed with a gradient of methanol in chloroform as eluent to yield pure target compound.

EXAMPLE 14

Synthesis of 1-O-octadecyl-sn-glycero-3-thiophosphonoacetate

A solution of 1-O-octadecyl-2-O-benzyl-sn-glycero-3-phosphonoacetic acid ethyl ester (1 mmol) in ethanol (50 ml) was combined with Pd/C (100 mg) and cyclohexene (5 ml) and the mixture was hydrogenated at 60 psi hydrogen overnight.

The mixture was filtered, and the filtrate concentrated in vacuo. The residue was flash chromatographed with a gradient of methanol in chloroform as eluent to yield the debenzylated ethyl ester. This was dissolved in a 1:1 mixture of ethanol and 0.1N NaOH (50 ml), and sonicated for 15 minutes. The mixture was heated at 60° for 2 h. The solution was filtered and concentrated in vacuo. The product was recrystallized from aqueous ethanol.

The following examples refer to the intermediate and target compounds numbered as shown in synthesis Schemes II and III.

EXAMPLE 15

Synthesis of Phosphonoacid Species Wherein Y=$CH_2$—OH, m=1, R1=octadecyl (Compound #8 on Scheme II)

D-erythrose, 1, (purchased from Aldrich Chemical Company), upon treatment with NaH and benzyl bromide in DMF at −70° C. will give the selectively protected species 4-O-benzyl-erythrose, 2. Treatment of this intermediate with dimethoxypropane and acetone with trace amounts of perchloric acid will lead to 2,3-di-O-isopropylidine-4-O-benzyl erythrose 3. Reduction of compound 3 with sodium borohydride leads to the protected erythritol, 4. Treatment of 4 with octadecylmethanesulfonate yields the 1-O-octadecyl-2,3,di-O-isopropylidine-4-O-benzyl erythritol 5. Debenzylation with Pd/C and hydrogen followed by DCC coupling with ethyl phosphonoformate will yield intermediate 7. Deblocking of 1 with 10% TFA in $CH_2Cl_2$ followed by base hydrolysis yields target compound 8.

EXAMPLE 16

Synthesis of Phosphonoformate Derivative Wherein $R_2$=H, Y=$CH_2$—OH, R=octadecyl, m=2 (Compound 17 on Scheme III)

Commercially available D-ribose, 9, (Sigma Chemical Co) upon treatment with trimethylsilyl methylmercaptan by adaptation of a procedure by Evans and Co-workers (Evans, D. A., Truesdale, L. K., Gimm, K. G., Nesbitt, S. L., J. Am. Chem. Soc., 99, 5009, 1977) will result in the dimethyldithioacetal 10. This locks the ribose in the open chain conformation. Treatment of the protected ribose with benzyl bromide in DMF at −70° will result in selective blocking of the 5-primary hydroxyl group of ribose leading to compound 11. Such selective blocking has been reported in the literature (1987, Fukuzawa, A., Sato, H., Masamune, T. Tetrahedron Lett. 28, 4303). The 2,3, and 4 hydroxyl groups on the 1,5 derivatized ribose can be protected by treatment with methoxymethyl chloride (1972, Stark, G., Takashi, T. J. Am. Chem. Soc., 94, 7827) to yield the fully protected ribose intermediate 12.

The aldehyde at the $C_1$ position is regenerated by treatment of intermediate 12 with $AgNO_3/Ag_2O$ (1977, Corey, E. J., Shibasaki, M., Knolle, J., Sugahara, T. Tetrahedron Lett., 785) to yield compound 13. Reduction with sodium borohydride followed by alkylation with octadecylmethanesulfonate yields the 1-O-octadecyl-2,3,4-tri-O-methoxymethyl-5-O-benzyl ribose 15.

Removal of the benzyl group by hydrogenation with Pd/C followed by coupling with ethyl phosphonoformate using dicyclohexyl carbodiimide yields the intermediate 16. Treatment with acetic acid removes the methoxymethyl protecting groups, and treatment with base leads to the target compound, 17.

SCHEME I
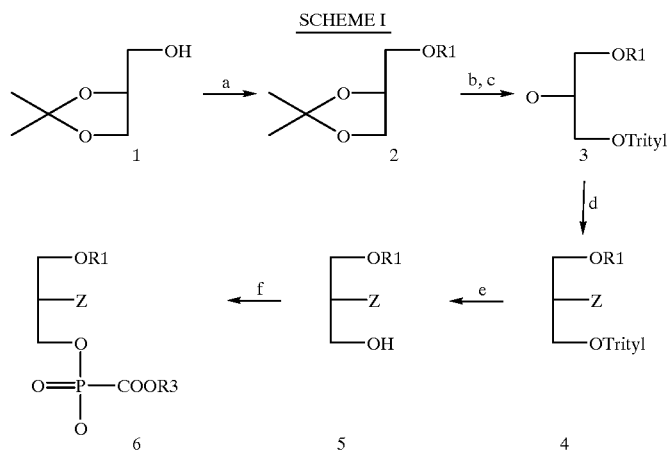
R1 = —(CH$_2$)$_n$CH$_3$, n = 7, 9, 11, 13, 15, 17
Z = Cl, Br, I, —OCH$_3$, —NH$_2$, —NH—R2, —N—(R2)$_2$
R = —CH$_3$, —CH$_2$CH$_3$ and —CH$_2$CH$_2$CH$_3$
a: NaH, DMF, R$_1$—OSO$_2$Me; b: Acetic acid; c: Trityl chloride, pyridine;
d: NaH, DMF, R$_2$—Br; e: TFA, CH$_2$Cl$_2$; f: Cl$_2$POCOOR$_3$, H$_2$O
SCHEME II
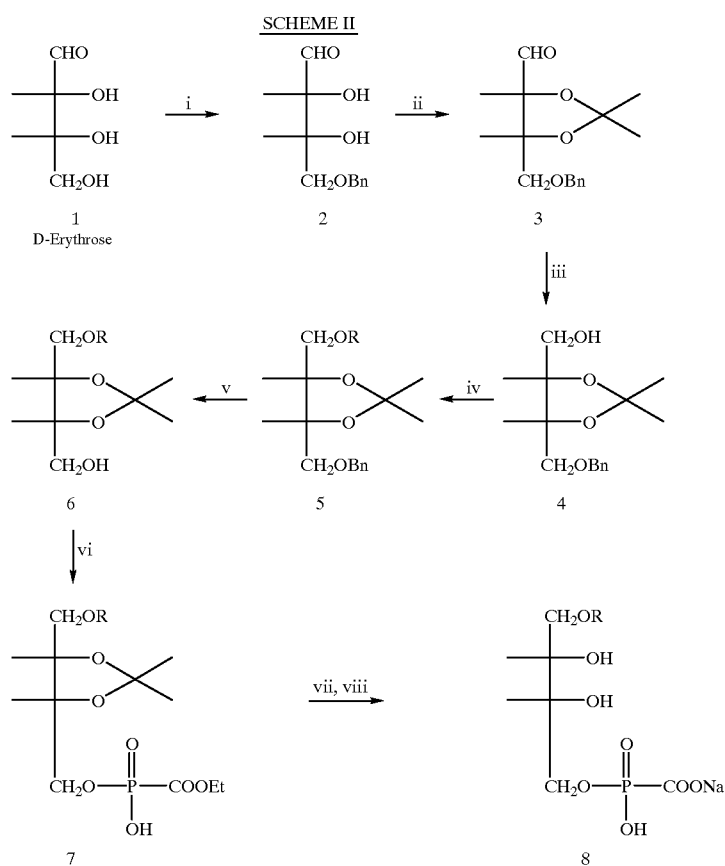
Example: Synthesis of phosphonoformic acid analog Y = CH$_2$OH,
m = 1, R2 = OH, R1 = Octadecyl -continued i. BnBr, NaH;
ii. DMP, H+;
iii. NaBH4;
iv. ROSO2Me (R=Octadecyl), NaH;
v. H2, Pd/C;
vi. DCC, ethyl phosphonoformate;
vii. TFA, CH2Cl2;

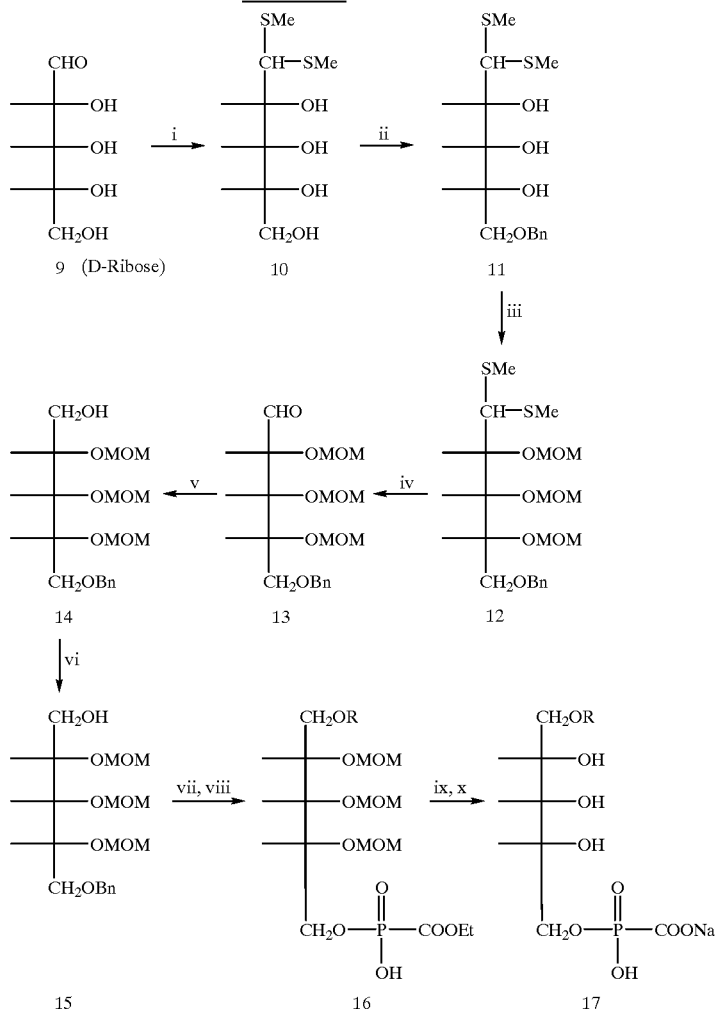

SCHEME III

Example: Synthesis of phosphonoformic acid analog Y = CH2OH, $m = 2$, R2 = OH, R1 = Octadecyl i. MeSSMe3, ZnI2;
ii. BnBr, NaH;
iii. CH3OCH2Cl (MOM chloride), NaH, THF;
iv. AgNO3, Ag2O;
v. NaBH4;
vi. ROSO2Me, NaH;
vii. H2, Pd/C;
viii. DCC, ethyl phosphonoformate;
ix. Acetic acid;
x. NaOH, ethanol

EXAMPLE 17

Antiviral Activity of Phosphonoacid Prodrugs in Cell Culture

Phosphonoacid derivatives having structures according to formula I were tested for antiviral activity in human embryonic lung fibroblasts (MRC-5) or in human epithelioid cervical carcinoma cells (HeLa) expressing the CD4 receptor (HT4-6C). HCMV (strain AD-169) and HSV-1 (wild type) were used to infect MRC-5 cells and HCMV or HSV-specific DNA was measured by DNA-probe methods (Hybriwix™, Diagnostic Hybrids, Inc., Athens, Ohio) according to the manufacturer's instructions. HIV replication was accessed in HIV-1 infected HT4-6C cells using a plaque reduction assay (Larder, B. et al. (1990) Antimicrobial Agents Chemother. 34:436).

The cytotoxicity of B-PFA and B-PAA in subconfluent MRC-5 cells was assessed by trypan blue exclusion. The toxic dose, $TD_{50}$ was >1000 $\mu$M and for B-PAA was 32–100 $\mu$M, indicating that the compounds have selectivity indexes which are 300 or greater.

EXAMPLE 18

CMV Antiviral Susceptibility Assay

Subconfluent MRC-5 cells in 24-well culture dishes were pretreated for 24 hours with various concentrations of drug in MEM medium containing 2% FBS and antibiotics. The media was removed and virus added at a dilution that will result in a 3–4+ cytopathic effect (CPE) in the no-drug wells in five days. This was absorbed for 1 hour at 37° C., aspirated and replaced with the drug dilutions. After five days of incubation HCMV DNA was quantified in triplicate by nucleic acid hybridization using a CMV Antiviral Susceptibility Test Kit from Diagnostic Hybrids, Inc. (Athens, Ohio). The media was removed and cells lysed according to the manufacturer's instructions. After absorption of the lysate, the Hybriwix™ filters were hybridized overnight at 60° C. The Hybriwix™ were washed for 30 minutes at 73° C. and counted in a gamma counter. The results are expressed as a percentage of the untreated HCMV-infected control cells.

EXAMPLE 19

HSV Antiviral Susceptibility Assay

Subconfluent MRC-5 cells in 24-well culture dishes were inoculated by removing the media and adding HSV-1 virus at a dilution that will result in a 3–4+ CPE in the no-drug well in 20–24 hours. This was absorbed for 1 hour at 37° C., aspirated and replaced with various concentrations of drugs in MEM medium containing 2% FBS and antibiotics. After approximately 24 hours of incubation, HSV DNA was quantified in triplicate by nucleic acid hybridization using a HSV Antiviral Susceptibility Test Kit from Diagnostic Hybrids, Inc. (Athens, Ohio). The media was removed and cells lysed according to the manufacturer's instructions. After absorption of the lysate, the Hybriwix™ filters were hybridized overnight at 60° C. The Hybriwix™ were washed for 30 minutes at 73° C. and counted in a gamma counter. The results are expressed as a percentage of the untreated HSV-infected control cells.

EXAMPLE 20

HT4-6C Cells

HT4-6C cells and plaque reduction assay, CD4-expressing HeLa cells, HT4-6C cells (Chesebro, B. and K. Wehrly (1988) J. Virology 62:3779–3788), were obtained from Bruce Chesebro, Hamilton, Mont. The effect of antiviral compounds on HIV replication was measured by a plaque reduction assay. Briefly, monolayers of HT4-6C cells were infected with 100 to 300 PFU of virus per well in 24-well microdilution plates. Various concentrations of drug were added to the culture medium, Dulbecco's Modified Eagle Medium containing 5% fetal bovine serum and antibiotics, as noted above. After 3 days at 37° C., the monolayers were fixed with 10% formaldehyde solution in phosphate-buffered saline and stained with 0.25% crystal violet to visualize virus plaques (Larder, B. et al. (1989) Science 243:1731–1734). Antiviral activity was assessed as the percentage of control plaques measured in drug-treated samples.

TABLE I

ANTI-HUMAN CYTOMEGALOVIRUS ACTIVITY OF PHOSPHONOFORMIC ACID AND VARIOUS PRODRUGS

| Compound | $IC_{50}$, $\mu$M (n) | | -fold increase in activity | p value |
|---|---|---|---|---|
| PFA | 46 ± 19 | (4) | — | — |
| B-PFA | 0.43 ± 0.27 | (9) | 107 | <0.0001 |
| BB-PFA | 0.64 ± 0.65 | (8) | 72 | <0.0001 |
| B-PFA-OEt | 1.2 ± 0.49 | (4) | 38 | 0.0016 |
| BB-PFA-OEt | 2.9 ± 0.97 | (4) | 16 | 0.0020 |
| MB-PFA | 0.64 ± 0.14 | (3) | 72 | 0.0050 |
| DMG-PFA | 125 ± 43 | (5) | 0.33 | 0.0058 |
| DMG-PFA-OEt | 30 ± 18 | (4) | 1.53 | 0.1337 |

ABBREVIATIONS: PFA, phosphonoformic acid; B-PFA, 1-O-octadecyl-sn-glycero-3-phosphonoformic acid; BB-PFA, 1-O-octadecyl-2-O-benzyl-sn-glycero-3-phosphonoformic acid; B-PFA-OEt, 1-O-octadecyl-sn-glycero-3-phosphonoformate ethyl ester; BB-PFA-OEt, 1-O-octadecyl-2-O-benzyl-sn- glycero-3-phosphonoformate ethyl ester; MB-PFA, 1-O-octadecyl-2-O-methyl-sn-glycero-3-phosphonoformic acid; DMG-PFA, 1,2-dimyristoyl-sn-glycero-3-phosphonoformate; DMG-PFA-OEt, 1,2-dimyristoyl-sn-glycero-3-phosphonoformate ethyl ester.

TABLE II

ANTI-HUMAN CYTOMEGALOVIRUS ACTIVITY OF PHOSPHONOACETIC ACID AND PHOSPHONOACETATE PRODRUGS

| Compound | $IC_{50}$, $\mu$M (n) | | -fold increase in activity | p value |
|---|---|---|---|---|
| PAA | 22 ± 7 | (5) | — | — |
| B-PAA | 0.22 ± 0.08 | (8) | 100 | <0.0001 |
| BB-PAA | 0.92 ± 0.80 | (7) | 24 | <0.0001 |
| B-PAA-OEt | 3.6 ± 1.5 | (7) | 6.1 | <0.0001 |
| BB-PAA-OEt | 7.2 ± 1.0 | (3) | 3.1 | <0.0062 |
| BB-(C)-PAA | 1.4 ± 0.9 | (3) | 16 | 0.0013 |
| MB-PAA | 0.61 ± 0.76 | (6) | 36 | <0.0001 |
| MB-PAA-OEt | 6.7 ± 1.9 | (3) | 3.3 | 0.0057 |
| DMG-PAA | 19 ± 6.5 | (4) | 1.2 | 0.2651 |
| DMG-PAA-OEt | 108 ± 42 | (3) | 0.2 | 0.0016 |
| DMP-PAA | 93 ± 92 | (3) | 0.2 | 0.0593 |
| DMP-PAA-OEt | 130 ± 28 | (2) | 0.2 | 0.0001 |
| DPP-PAA | 80 ± 42 | (2) | 0.3 | 0.0086 |

ABBREVIATIONS: PAA, phosphonoacetic acid; B-PAA, 1-O-octadecyl-sn-glycero-3-phosphonoacetic acid; BB-PAA, 1-O-octadecyl-2-O-benzyl-sn-glycero-3-phosphonoacetic acid; B-PAA-OEt, 1-O-octadecyl-sn-glycero-3-phosphonoacetate ethyl ester; BB-PAA-OEt, 1-O-octadecyl-2-O-benzyl-sn-glycero-3-phosphonoacetate ethyl ester; BB-(C)-PAA, 1-O-octadecyl-2-O-benzyl-sn-glycero-3-carboxymethylenephosphonate; MB-PAA, 1-O-octadecyl-2-O- methyl-sn-glycero-3-phosphonoacetic acid; DMG-PAA, 1,2-dimyristoyl-sn-glycero-3-phosphonoacetate; DMG-PAA-OEt, 1,2-dimyristoyl-sn-glycero-3-phosphonoacetate ethyl ester; DMP-PAA, 1,2-dimyristoyl-sn-glycero-3-phospho-phosphonoacetate; DMP-PAA-OEt, 1,2-dimyristoyl-sn-glycero-3-phospho-phosphonoacetate ethyl ester; DPP-PAA, 1,2-dipalmitoyl-sn-glycero-3-phospho-phosphonoacetate.

TABLE III

INHIBITION OF HUMAN HERPES SIMPLEX VIRUS 1 REPLICATION BY PHOSPHONOFORMATE AND PHOSPHONOFORMATE PRODRUGS

| Compound | IC$_{50}$, µM (n) | | -fold increase in activity | p value |
|---|---|---|---|---|
| PFA | 47 ± 20 | (6) | — | — |
| B-PFA | 1.1 ± 1.1 | (5) | 43 | 0.0003 |
| BB-PFA | 1.4 ± 0.4 | (4) | 34 | 0.0003 |
| MB-PFA | 0.65 ± 0.21 | (4) | 72 | 0.0009 |

Data are Mean ± S.D.
Number in parentheses (n) is the number of replicates.
P values versus PFA were determined by student's T test using Instat2 Statistical Software (Graph Pad Software, San Diego, CA).
ABBREVIATIONS: PFA, phosphonoformic acid;. B-PFA, 1-O-octadecyl-sn-glycero-3-phosphonoformic acid; BB-PFA, 1-O-octadecyl-2-O-benzyl-sn-glycero-3-phosphonoformic acid; MB-PFA, 1-O-octadecyl-2-O-methyl-sn-glycero-3-phosphonoformic acid.

TABLE IV

ANTIVIRAL EFFECT OF PHOSPHONOFORMATE AND PHOSPHONOFORMATE PRODRUGS ON HUMAN IMMUNODEFICIENCY VIRUS-1 REPLICATION IN HT4-6C CELLS

| Compound | IC$_{50}$, µM (n) | | -fold increase in activity | p value |
|---|---|---|---|---|
| PFA | 133 ± 54 | (8) | — | — |
| B-PFA | 3.60 ± 1.51 | (3) | 37 | 0.0015 |
| BB-PFA | 14.8 ± 7.3 | (2) | 9.0 | 0.0091 |
| MB-PFA | 1.28 ± 0.73 | (3) | 104 | 0.0014† |

†p = 0.0373 versus B-PFA
Data are Mean ± S.D.
Number in parentheses (n) is the number of replicates.
P values versus PFA were determined by student's T test of unpaired means using Instat2 Statistical Software (Graph Pad Software, San Diego, CA).
ABBREVIATIONS: PFA, phosphonoformic acid; B-PFA, 1-O-octadecyl-sn-glycero-3-phosphonoformic acid; BB-PFA, 1-O-octadecyl-2-O-benzyl-sn-glycero-3-phosphonoformic acid; MB-PFA, 1-O-octadecyl-2-O-methyl-sn-glycero-3-phosphonoformic acid.

The invention may be embodied in other specific forms without departing from its spirit of essential characteristics. The described embodiments are to be considered in all respects only as illustrative and not restrictive, and the scope of the invention is therefore indicated by the appended claims rather than by the foregoing description. All modifications which come within the meaning and range of the lawful equivalency of the claims are to be embraced within their scope.

What is claimed is:

1. A compound of the formula

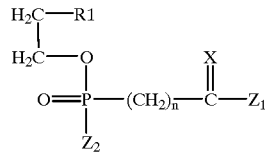

wherein
R1 is
(a) O—(C$_1$ to C$_{24}$)alkyl;
(b) S—(C$_1$ to C$_{24}$)alkyl;
(c) O—(C$_2$ to C$_{24}$)alkenyl;
(d) S—(C$_2$ to C$_{24}$)alkenyl;
(e) O—C(O)—(C$_1$ to C$_{24}$)alkyl;
(f) S—C(O)—(C$_1$ to C$_{24}$)alkyl;
(g) O—C(O)—(C$_2$ to C$_{24}$)alkenyl; or
(h) S—C(O)—(C$_2$ to C$_{24}$)alkenyl;
wherein said alkyl or alkenyl group is linear or branched, substituted or unsubstituted, and wherein said alkenyl group has from 1 to 6 double bonds;
X is O, S or Se;
Z1 and Z2 are independently OR3 or O$^-$A$^+$; wherein
R3 is independently selected from the group consisting of substituted or unsubstituted
(i) (C$_1$ to C$_6$)alkyl, linear;
(j) (C$_1$ to C$_6$)alkyl, branched;
(k) CH$_2$-phenyl; and
(l) CH$_2$(CH$_2$)$_n$ NH$_2$; wherein n is 0 to 8; or
R3 is selected from the group consisting of
(m) CH$_2$CH$_2$N$^+$(CH$_3$)$_3$;
(n) CH$_2$CH$_2$NH$_2$;
(o) CH$_2$CH(NH$_2$)CO$_2$H;
(p) C$_6$H$_{12}$O$_5$;
(q) CHCHOHCH$_2$OH;
and corresponding radicals derived from the alcohols of pentoses and hexoses;
A$^+$ is selected from the group consisting of
(a) H$^+$;
(b) K$^+$;
(c) Na$^+$;
(d) NH$_4^+$; and
(e) amines selected from the group consisting of mono-, di-, and trialkylamines; and other physiologically acceptable cations;
X is O, S or Se; and
n=0 or 1.

2. A compound according to claim 1 which is a 1-O-alkyl-1,2-ethanediol-2-phosphonoacid or a physiologically acceptable salt or ester of said compound.

3. A compound according to claim 2 which is a 1-O-alkyl-1,2-ethanediol-2-phosphonoacetate or a physiologically acceptable salt or ester of said compound.

4. A compound according to claim 2 which is a 1-O-alkyl-1,2-ethanediol phosphonoformate or a physiologically acceptable salt or ester of said compound.

5. A 1-O-hexadecyl-1,2-ethanediol phosphonoformate methyl ester according to claim 4.

6. A 1-O-octadecyl-1,2-ethanediol phosphonoformate methyl ester according to claim 4.

7. A 1-O-eicosanyl-1,2-ethanediol phosphonoformate methyl ester according to claim 4.

8. A compound of the formula

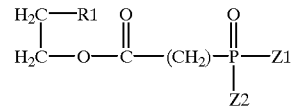

wherein
R1 is
(a) O—(C$_1$ to C$_{24}$)alkyl;
(b) S—(C$_1$ to C$_{24}$)alkyl;
(c) O—(C$_2$ to C$_{24}$)alkenyl;
(d) S—(C$_2$ to C$_{24}$)alkenyl;
(e) S—C(O)—(C$_1$ to C$_{24}$)alkyl;
(f) O—C(O)—(C$_2$ to C$_{24}$)alkenyl; or
(g) S—C(O)—(C$_2$ to C$_{24}$)alkenyl;
wherein said alkyl or alkenyl group is linear or branched, substituted or unsubstituted, and wherein said alkenyl group has from 1 to 6 double bonds;
X is O, S or Se;

Z1 and Z2 are independently OR3 or $O^{-A+}$; wherein
R3 is selected from the group consisting of substituted or unsubstituted
- (a) ($C_1$ to $C_6$)alkyl, linear;
- (b) ($C_3$ to $C_6$)alkyl, branched;
- (c) $CH_2$-phenyl; and
- (d) $CH_2(CH_2)_n NH_2$ wherein n is 0 to 8; or R3 is selected from the group consisting of
- (e) $CH_2(CH_2)_n NH_2$;
- (f) $CH_2CH_2OH$;
- (g) $CH_2CH_2NH_2$;
- (h) $CH_2CH_2(NH_2)CO_2H$;
- (i) $C_6H_{12}O_5$;

and corresponding radicals derived from the alcohols of pentoses and hexoses;

$A^+$ is selected from the group consisting of
- (a) $H^+$;
- (b) $K^+$;
- (c) $Na^+$;
- (d) $NH_4^+$; and
- (e) amines selected from the group consisting of mono-, di-, and trialkylamines; and other physiologically acceptable cations;

X is O, S or Se; and n=0 or 1.

9. A compound according to claim 8 that is a 1-O-alkyl-1,2-ethanediol-2(C)-phosphonoacid or a physiologically acceptable salt or ester of said compound.

10. A compound according to claim 9 that is a 1-O-octadecyl-1,2-ethanediol-2-(C)-phosphonoacid or a physiologically acceptable salt or ester of said compound.

11. A compound according to claim 8 that is a 1-O-alkyl-1,2-ethanediol-2(C)-phosphonoacetate or a physiologically acceptable salt or ester of said compound.

12. A compound according to claim 8 that is a 1-O-alkyl-1,2-ethanediol-2(C)-phosphonoformate or a physiologically acceptable salt or ester of said compound.

13. A compound according to claim 1 or 8 wherein R1 is an O-alkyl group and; wherein Z1 is an OR3 group O-alkyl selected from the group consisting of choline, ethanolamine, glycerol and inositol and Z2 is $O^-A^+$ wherein $A^+$ is a physiologically acceptable ion.

14. A liposome formed in part from a compound according to claim 1 or 8.

15. A pharmaceutical formulation comprising any of the compounds of claim 1 or 8.

16. A method for treating a viral or retroviral infection in a mammal in need thereof comprising administering an effective antiviral amount of a compound according to claim 1 or 8 to said mammal.

17. A method according to claim 16 further comprising the co-administration of an antiviral nucleoside analogue, viral protease inhibitor, or other antiviral agent to said mammal.

* * * * *